(12) United States Patent
Shluzas

(10) Patent No.: US 6,837,889 B2
(45) Date of Patent: Jan. 4, 2005

(54) APPARATUS FOR CONNECTING A LONGITUDINAL MEMBER TO A BONE PORTION

(75) Inventor: Alan E. Shluzas, Millis, MA (US)

(73) Assignee: Endius Incorporated, Plainville, MA (US)

( * ) Notice: Subject to any disclaimer, the term of this patent is extended or adjusted under 35 U.S.C. 154(b) by 0 days.

(21) Appl. No.: 10/087,489

(22) Filed: Mar. 1, 2002

(65) Prior Publication Data

US 2003/0167058 A1 Sep. 4, 2003

(51) Int. Cl.⁷ .............................................. A61B 17/58
(52) U.S. Cl. ...................................................... 606/61
(58) Field of Search ............................. 606/61, 72, 73, 606/60

(56) References Cited

U.S. PATENT DOCUMENTS

| | | | |
|---|---|---|---|
| 5,207,678 A | | 5/1993 | Harms et al. |
| 5,443,467 A | | 8/1995 | Biedermann et al. |
| 5,672,176 A | * | 9/1997 | Biedermann et al. ......... 606/61 |
| 5,885,286 A | | 3/1999 | Sherman et al. |
| 6,077,262 A | | 6/2000 | Schlapfer et al. |
| 6,113,601 A | | 9/2000 | Tatar |
| 6,280,442 B1 | | 8/2001 | Barker et al. |
| 6,287,311 B1 | | 9/2001 | Sherman et al. |
| 6,302,888 B1 | * | 10/2001 | Mellinger et al. ............ 606/73 |
| 6,440,137 B1 | * | 8/2002 | Horvath et al. ............... 606/73 |
| 6,485,491 B1 | * | 11/2002 | Farris et al. ................... 606/61 |

OTHER PUBLICATIONS

U.S. Shluzas patent application Ser. No. 10/075,668, filed Feb. 13, 2002 entitled An Apparatus For Connecting a Longitudinal Member to a Bone Portion.

\* cited by examiner

*Primary Examiner*—Eduardo C. Robert
*Assistant Examiner*—Anuradha Ramana
(74) *Attorney, Agent, or Firm*—Tarolli, Sundheim, Covell & Tummino L.L.P.

(57) ABSTRACT

A housing (40) has a first passage (42) through which a longitudinal member (12) extends and a second passage (44) extending transverse to the first passage. A fastener (16) extends through an opening (50) in the housing (40) into the second passage (44). An axis (18) of the fastener (16) is positionable in any one of a plurality of angular positions relative to an axis (46) of the second passage (44). A spacer (60) received in the second passage (44) engages the fastener (16) and the longitudinal member (12). A pin member (70) fixedly connected to the housing (40) extends into engagement with the spacer (60) to retain the spacer and the fastener (16) in the housing and maintain the spacer in frictional engagement with the fastener to prevent relative movement between the fastener (16) and the housing when the longitudinal member (12) is disengaged from the spacer. The fastener (16) and the housing (40) are manually movable relative to each other in opposition to the frictional engagement. A clamping mechanism (90) clamps the longitudinal member (12), the spacer (60), and the housing (40) to the fastener (16) to prevent movement of the fastener relative to the housing.

38 Claims, 3 Drawing Sheets

APPARATUS FOR CONNECTING A LONGITUDINAL MEMBER TO A BONE PORTION

TECHNICAL FIELD

The present invention relates to an apparatus which is used to retain bone portions, such as vertebrae of a spinal column, in a desired spatial relationship.

BACKGROUND OF THE INVENTION

A known apparatus for retaining vertebrae of a spinal column in a desired spatial relationship is disclosed in U.S. Pat. No. 6,280,442. U.S. Pat. No. 6,280,442 discloses an apparatus including a longitudinal member extendable along the spinal column. A fastener engageable with a vertebra of the spinal column connects the longitudinal member to the vertebra. A housing has a first passage through which the longitudinal member extends and a second passage with a longitudinal axis extending transverse to the first passage. The fastener extends through an opening in the housing into the second passage. The longitudinal axis of the fastener is positionable in any one of a plurality of angular positions relative to the longitudinal axis of the second passage.

A spacer received in the housing is engageable with the fastener and the longitudinal member. A retaining ring holds the spacer and the housing on the fastener when the rod is disengaged from the spacer. A clamping member threadably engages the housing to clamp the longitudinal member, the spacer, and the housing to the fastener to prevent movement of the fastener relative to the housing. When the longitudinal member is disengaged from the spacer, the housing may not remain in position relative to the fastener until the longitudinal member is clamped to the spacer.

SUMMARY OF THE INVENTION

The present invention is an apparatus which is used to retain bone portions in a desired spatial relationship. The apparatus includes a longitudinal member connectable with a bone portion. A fastener having a longitudinal axis is engageable with the bone portion to connect the longitudinal member to the bone portions A housing has a first passage through which the longitudinal member extends. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage.

A spacer received in the second passage of the housing is engageable with the fastener and the longitudinal member. A pin member fixedly connected to the housing extends from the housing and into engagement with the spacer to retain the spacer and the fastener in the housing. The pin member also maintains the spacer in frictional engagement with the fastener to prevent relative movement between the fastener and the housing when the longitudinal member is disengaged from the spacer and the spacer engages the fastener. The fastener and the housing are manually movable relative to each other in opposition to the frictional engagement when the longitudinal member is disengaged from the spacer. A clamping mechanism clamps the longitudinal member, the spacer, and the housing to the fastener to prevent movement of the fastener relative to the housing. Accordingly, the housing and the fastener can be positioned relative to each other and the member will hold the fastener and the housing in the relative positions before the longitudinal member is connected to the housing.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DESCRIPTION OF THE INVENTION

Figure 1:
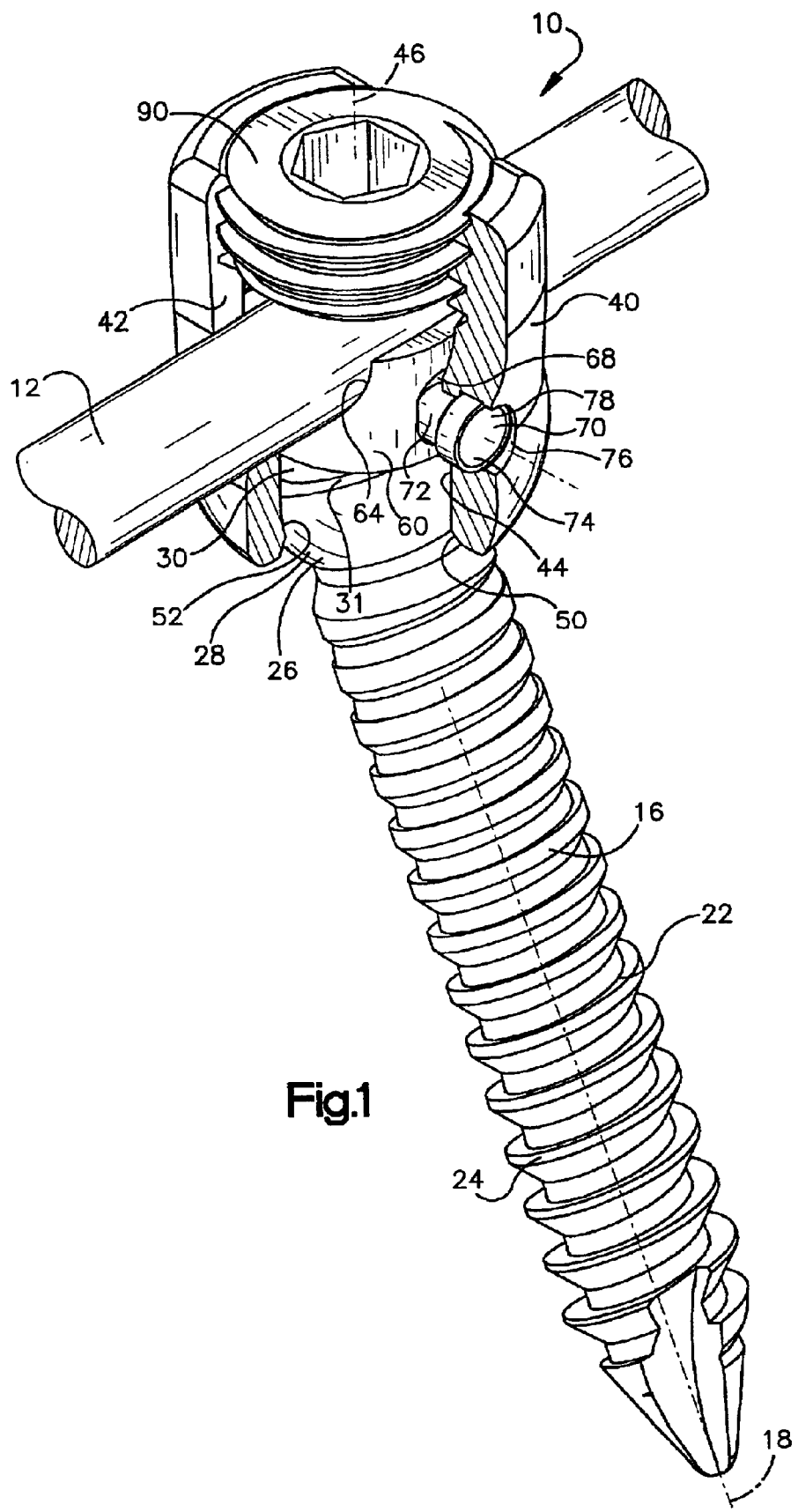
FIG. 1 is a perspective view of an apparatus constructed in accordance with the present invention with portions removed for clarity.
Figure 2:
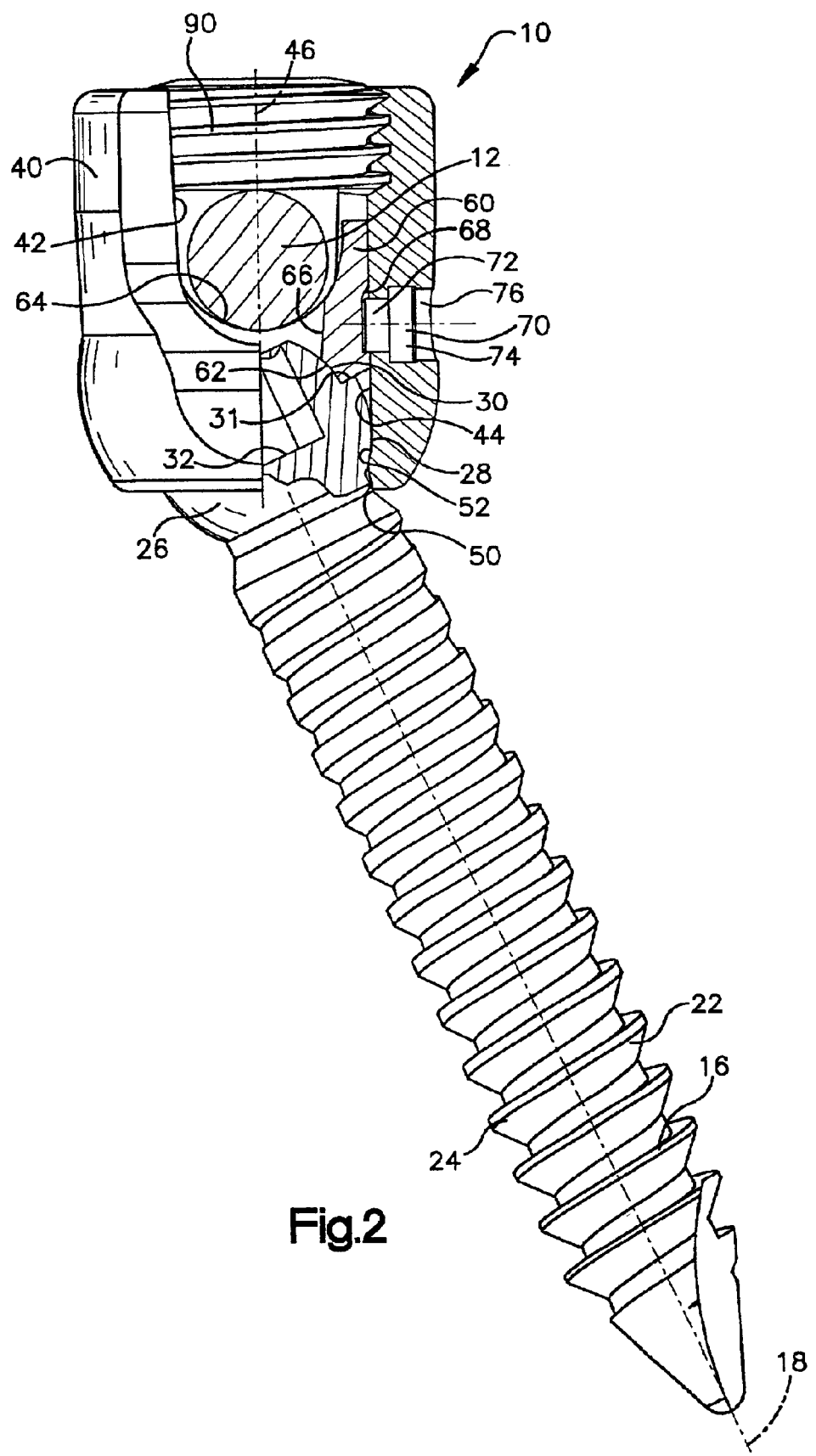
FIG. 2 is a part sectional view of the apparatus of FIG. 1.
Figure 3:
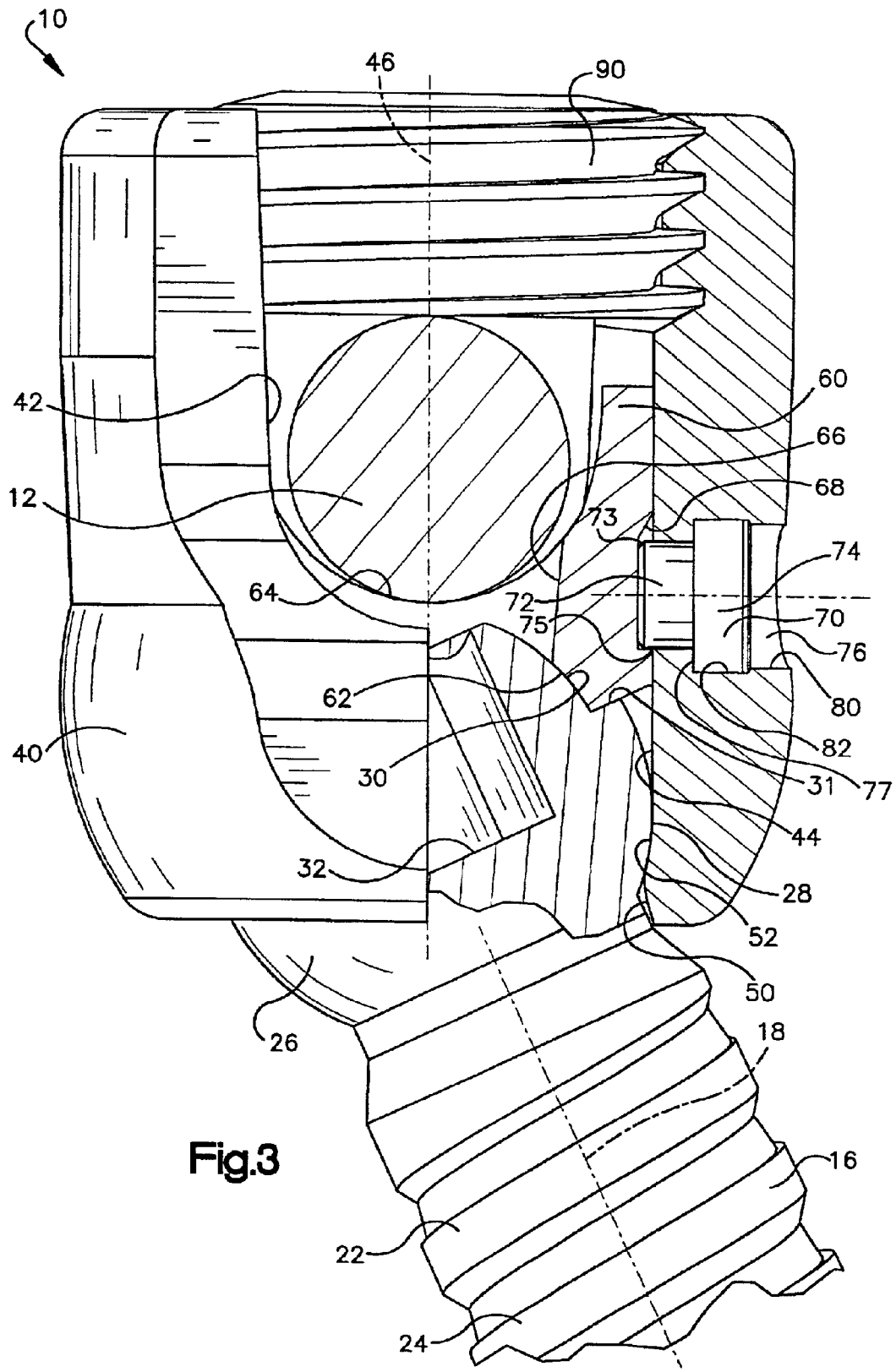
FIG. 3 is an enlarged part sectional view of a portion of the apparatus of FIG. 1.

The present invention is directed to an apparatus for retaining bone portions, such as vertebrae of a spinal column, in a desired spatial relationship. FIGS. 1–3 illustrate an apparatus 10 constructed according to the present invention. The apparatus 10 includes a surgically implantable longitudinal member or rod 12 for maintaining bone portions, such as vertebrae of a spinal column, in a desired spatial relationship. The rod 12 is connected with vertebrae of the spinal column by fasteners 16.

The rod 12 is made of a suitable biocompatible material and has a length which is at least sufficient to enable the rod to span at least two vertebrae. Of course, the length of the rod 12 in any particular installation will depend upon the condition to be corrected and the number of vertebrae to be held in a desired spatial relationship relative to each other by the rod.

The rod 12 is connected to a respective vertebra by the fastener 16 made of a suitable biocompatible material. The fastener 16 has a longitudinal axis 18 and a threaded end portion 22 having a course thread convolution 24 which engages the vertebra. A second end portion 26 (FIGS. 2–3) of the fastener 16 is provided with a first part spherical surface 28. The second end portion 26 of the fastener 16 also includes a second part spherical surface 30 having a diameter less than a diameter of the first part spherical surface 28. A radially extending shoulder 31 extends between the part spherical surfaces 28 and 30. A recess 32 (FIGS. 2–3) is provided on the end portion 26 of the fastener 16. The recess 32 receives a tool (not shown) that applies torque to the fastener 16 to turn the thread convolution 24 into the vertebra.

The fastener 16 (FIGS. 1–3) extends into a housing 40 that interconnects the rod 12 and the fastener 16. The housing 40 has a first passage 42 through which the rod 12 extends. The housing 40 has a second passage 44 with a longitudinal axis 46 that extends transverse to the first passage 42. The fastener 16 extends through an opening 50 in the housing 40 and into the second passage 44. The first part spherical surface 28 of the fastener 16 engages a concave part spherical surface 52 of the housing 40. Accordingly, the fastener 16 is universally pivotable relative to the housing 40 so that the longitudinal axis 18 of the fastener 16 is positionable in any one of a plurality of angular positions relative to the longitudinal axis 46 of the passage 44.

A spacer 60 is received in the second passage 44 of the housing 40. The spacer 60 (FIGS. 2–3) has a concave part spherical surface 62 that engages the part spherical surface 30 of the fastener 16. The spacer 60 also has a concave part cylindrical surface 64 that engages the rod 12. The spacer 60 has an opening 66 through which the tool (not shown) extends to engage the recess 32 in the fastener 16. The tool extends through the opening 66 to apply torque to the fastener 16 and connect the fastener to the vertebra.

The spacer 60 has a pair of axially extending grooves 68, one of which is shown in FIGS. 1–3. The grooves 68 are located on diametrically opposite sides of the spacer 60. A pair of pin members 70, one of which is shown in FIGS. 1–3, extend transverse to the longitudinal axis 46 of the passage 44 and through the housing 40 into the grooves 68 and into engagement with the spacer 60. The pin members 70 retain the spacer 60 and the fastener 16 in the housing 40.

The pin members 70 are identical and, therefore, only one pin member will be described in detail. The pin member 70 has a first cylindrical end portion 72 that extends into the groove 68 and engages the spacer 60. The end portion 72 of the pin member 70 has a frustoconical or tapered surface 73. The tapered surface 73 engages a lower axial edge 75 that defines the groove 68 as the pin member 70 is being inserted through the housing 40 to urge the spacer axially toward the fastener 16. The pin member 70 urges the spacer 60 into frictional engagement with the fastener 16 and the fastener into frictional engagement with the housing 40. It is contemplated that the pin member 70 may not urge the spacer 60 axially toward the fastener 16 and only retain the spacer and the fastener in the housing 40.

A second cylindrical end portion or head 74 of the pin member 70 is located in a cylindrical opening 76 in the housing 40. The head 74 has a diameter greater than a diameter of the end portion 72. Accordingly, the pin member 70 (FIG. 3) has a shoulder surface 77 extending perpendicular to the axis of the pin member 70 on the head 74. The shoulder surface 77 engages the housing 40 to limit the distance that the pin member 70 extends into the housing 40.

The head 74 of the pin member 70 has a conical recess 78 (FIG. 1) for receiving a tool (not shown), such as a center punch, to deform the head 74 into engagement with the housing 40. The opening 76 (FIG. 3) in the housing 40 has a radially outer portion 80 with a diameter slightly smaller than a diameter of a radially central portion 82 of the opening. The head 74 of the pin member 70 is received in the radially central portion 82 of the opening 76. The material of the head 74 is deformed into tight engagement with the material of the housing defining the central portion 82 of the opening 76 so that the diameter of the head is larger than the diameter of the radially outer portion 80 of the opening 76. Accordingly, the pin member 70 is fixedly connected to the housing 40. Although the pin member 70 is described as being deformed into engagement with the housing 40, it is contemplated that the pin member could be press fit into the housing or otherwise suitably fixed in the housing.

The pin members 70 engage the housing 40 and the spacer 60 to retain the spacer and the fastener in the housing 40. The pin members 70 also apply an axial force to the spacer 60 to prevent relative movement between the fastener 16 and the housing 40 when the rod 12 is disengaged from the spacer and the spacer engages the fastener. The pin members 70 hold the part spherical surface 62 of the spacer 60 in frictional engagement with the part spherical surface 30 of the fastener 16 and the part spherical surface 28 of the fastener in frictional engagement with the part spherical surface 52 of the housing 40. The frictional engagements are effective to maintain the housing 40 and the fastener 16 in position when the rod 12 is disengaged from the spacer. However, the fastener 16 and the housing 40 are manually movable relative to each other by a surgeon manually overcoming the frictional engagements when the rod 12 is disengaged from the spacer 60 and the pin members 70 engage the spacer. Accordingly, the housing 40 can be positioned relative to the fastener 16 and held in position relative to the fastener by the pin members 70 without the rod 12 engaging the spacer 60. Furthermore, the spacer 60 and the fastener 16 are retained in the housing 40 by the pin members 70 and with the rod 12 disengaged from the spacer.

A clamping mechanism or set screw 90 (FIGS. 1–3) threadably engages the housing 40. The set screw 90 and the housing 40 have a German standard DIN513 buttress thread. It is contemplated that the housing 40 and the set screw 90 could have any desired thread formation. The set screw 90 engages the rod 12 to press the rod against the spacer 60 and the spacer against the fastener 16. The set screw 90 clamps the rod 12, the spacer 60, and the housing 40 to the fastener 16 to prevent movement of the fastener relative to the housing.

The apparatus 10 is assembled by inserting the fastener 16 through the opening 50 in the housing 40 so that the part spherical surface 28 of the fastener engages the part spherical surface 52 of the housing. The spacer 60 is inserted into the second passage 44 of the housing 40 until the part spherical surface 62 of the spacer engages the part spherical surface 30 of the fastener 16. The pin members 70 are inserted into the openings 76 in the housing 40 until the end portions 72 extend into the grooves 68 in the spacer 60 and engage the spacer. The tapered surfaces 73 of the pin members 70 engage the edges 75 to urge the spacer 60 axially toward the fastener 16. The heads 74 of the pins 70 are deformed to fixedly connect the pins to the housing 40.

A tool is inserted through the opening 66 in the spacer 60 and into the recess 32 in the fastener 16. Torque is applied to the fastener 16 to turn the thread convolution 24 into the vertebra. Once the fastener 16 is connected with the vertebra, the housing 40 can be positioned relative to the fastener. The pin members 70 and the above described frictional engagements maintain the position of the housing 40 relative to the fastener 16 while the rod 12 is disengaged from the spacer 60. Once the housing 40 is positioned relative to the fastener 16 as desired by the surgeon, the rod 12 is placed into the passage 42 and in engagement with the spacer 60. The set screw 90 is threaded into the housing 40 and into engagement with the rod 12. The set screw 90 clamps the rod 12, the spacer 60, and the housing 40 to the fastener 16 to prevent movement of the fastener relative to the housing.

It is contemplated that the pin members 70 could be inserted into the housing 40 prior to the spacer 60 being inserted into the housing. If the spacer 60 is inserted after the pin members 70, the spacer would have L-shaped grooves with axially extending portions and circumferentially extending portions. The spacer 60 would be inserted into the housing 40 with the axially extending portions aligned with the pin members 70 until the pin members extend into the circumferentially extending portions. The spacer 60 would be rotated relative to the housing 40 until the pin members 70 are located in ends of the circumferentially extending portions of the grooves opposite from the axially extending portions.

From the above description of the invention, those skilled in the art will perceive improvements, changes and modifications. Such improvements, changes and modifications within the skill of the art are intended to be covered by the appended claims.

What is claimed is:

1. An apparatus comprising:
   a longitudinal member connectable with a bone portion;
   a fastener engageable with the bone portion having a longitudinal axis and connecting said longitudinal member to the bone portion;
   a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
   a spacer received in said second passage of said housing and engageable with said fastener and said longitudinal member;
   a member fixedly connected to said housing and extending from said housing into engagement with said spacer, said member applying an axial force to said spacer to maintain said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer; and
   a clamping mechanism that clamps said longitudinal member, said spacer, and said housing to said fastener to prevent movement of said fastener relative to said housing.

2. An apparatus as defined in claim 1 wherein said fastener includes a first part spherical surface engageable with a part spherical surface of said housing.

3. An apparatus as defined in claim 2 wherein said fastener includes a second part spherical surface engageable with said spacer.

4. An apparatus as defined in claim 3 wherein said fastener includes a surface engageable with said spacer to limit relative movement between said fastener and said housing.

5. An apparatus as defined in claim 4 wherein said second part spherical surface has a diameter smaller than a diameter of said first part spherical surface, said surface engageable with said spacer to limit relative movement between said fastener and said housing extending between said first and second part spherical surfaces.

6. An apparatus as defined in claim 1 wherein said spacer has an opening through which a tool extends to engage said fastener when said longitudinal member is disengaged from said spacer.

7. An apparatus as defined in claim 1 wherein said clamping mechanism includes a threaded member threadably engageable with said housing.

8. An apparatus as defined in claim 7 wherein said threaded member engages said longitudinal member to clamp said longitudinal member against said spacer.

9. An apparatus as defined in claim 7 wherein said threaded member and said housing have a buttress thread.

10. An apparatus comprising:
    a longitudinal member connectable with a bone portion;
    a fastener engageable with the bone portion having a longitudinal axis and connecting said longitudinal member to the bone portion;
    a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
    a spacer received in said second passage of said housing and engageable with said fastener and said longitudinal member;
    a pin member fixedly connected to said housing and extending from said housing into engagement with said spacer to retain said spacer and said fastener in said housing when said longitudinal member is disengaged from said spacer; and
    a clamping mechanism that clamps said longitudinal member, said spacer, and said housing to said fastener to prevent movement of said fastener relative to said housing.

11. An apparatus as defined in claim 10 wherein said pin member maintains said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer.

12. An apparatus as defined in claim 10 wherein said pin member extends transverse to said longitudinal axis of said second passage.

13. An apparatus as defined in claim 10 wherein said pin member extends through said housing and into engagement with said spacer.

14. An apparatus as defined in claim 13 wherein said pin member has a first axial end portion with a first diameter that engages said spacer and a second axial end portion with a second diameter larger than said first diameter that engages said housing.

15. An apparatus as defined in claim 14 wherein said second axial end portion is deformed into engagement with said housing to fixedly connect said pin member to said housing.

16. An apparatus as defined in claim 13 wherein said spacer has a groove into which said pin member extends.

17. An apparatus as defined claim 10 wherein said fastener includes a first part spherical surface engageable with a part spherical surface of said housing and a second part spherical surface engageable with said spacer.

18. An apparatus as defined in claim 17 wherein said second part spherical surface has a diameter smaller than a diameter of said first part spherical surface, said fastener including a surface engageable with said spacer to limit relative movement between said fastener and said housing extending between said first and second part spherical surfaces.

19. An apparatus as defined in claim 10 wherein said spacer has an opening through which a tool extends to engage said fastener when said longitudinal member is disengaged from said spacer.

20. An apparatus as defined in claim 10 wherein said clamping mechanism includes a threaded member threadably engageable with said housing.

21. An apparatus as defined in claim 20 wherein said threaded member engages said longitudinal member to clamp said longitudinal member against said spacer.

22. An apparatus as defined in claim 20 wherein said threaded member and said housing have a buttress thread.

23. An apparatus comprising:
a longitudinal member connectable with a bone portion;
a fastener engageable with the bone portion having a longitudinal axis and connecting said longitudinal member to the bone portion;
a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
a spacer received in said second passage of said housing and engageable with said fastener and said longitudinal member;
a member fixedly connected to said housing and extending from said housing into engagement with said spacer to maintain said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer, said member being a pin member extending transverse to said longitudinal axis of said second passage; and
a clamping mechanism that clamps said longitudinal member, said spacer, and said housing to said fastener to prevent movement of said fastener relative to said housing.

24. An apparatus comprising:
a longitudinal member connectable with a bone portion;
a fastener engageable with the bone portion having a longitudinal axis and connecting said longitudinal member to the bone portion;
a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
a spacer received in said second passage of said housing and engageable with said fastener and said longitudinal member;
a member fixedly connected to said housing and extending from said housing into engagement with said spacer to maintain said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer, said member extending through said housing and into engagement with said spacer, said member having a first axial end portion with a first diameter that engages said spacer and a second axial end portion with a second diameter larger than said first diameter that engages said housing; and
a clamping mechanism that clamps said longitudinal member, said spacer, and said housing to said fastener to prevent movement of said fastener relative to said housing.

25. An apparatus as defined in claim 24 wherein said second axial end portion is deformed into engagement with said housing to fixedly connect said member to said housing.

26. An apparatus comprising:
a longitudinal member connectable with a bone portion;
a fastener engageable with the bone portion having a longitudinal axis and connecting said longitudinal member to the bone portion;
a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
a spacer received in said second passage of said housing and engageable with said fastener and said longitudinal member;
a member fixedly connected to said housing and extending from said housing into engagement with said spacer to maintain said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer, said member extending through said housing and into engagement with said spacer; and
a clamping mechanism that clamps said longitudinal member, said spacer, and said housing to said fastener to prevent movement of said fastener relative to said housing.

27. An apparatus as defined in claim 26 wherein said spacer has a groove into which said member extends.

28. An apparatus as defined in claim 26 wherein said member has a surface engageable with said spacer that urges said spacer axially toward said fastener and into frictional engagement with said fastener as said member is inserted through said housing.

29. An apparatus comprising:
a longitudinal member connectable with a bone portion;
a fastener engageable with the bone portion having a longitudinal axis and connecting said longitudinal member to the bone portion;

a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;

a spacer received in said second passage of said housing and engageable with said fastener and said longitudinal member;

a member fixedly connected to said housing and extending from said housing into engagement with said spacer to maintain said spacer in frictional engagement with said fastener, said member including means for preventing relative movement between said fastener and said housing when said longitudinal member is disengaged from said spacer and said spacer engages said fastener, said fastener and said housing being manually movable relative to each other upon application of a force in opposition to said frictional engagement when said longitudinal member is disengaged from said spacer; and a clamping mechanism that clamps said longitudinal member, said spacer, and said housing to said fastener to prevent movement of said fastener relative to said housing.

30. An apparatus as defined in claim 29 wherein said fastener includes a first part spherical surface engageable with a part spherical surface of said housing.

31. An apparatus as defined in claim 30 wherein said fastener includes a second part spherical surface engageable with said spacer.

32. An apparatus as defined in claim 31 wherein said fastener includes a surface engageable with said spacer to limit relative movement between said fastener and said housing.

33. An apparatus as defined in claim 32 wherein said second part spherical surface has a diameter smaller than a diameter of said first part spherical surface, said surface engageable with said spacer to limit relative movement between said fastener and said housing extending between said first and second part spherical surfaces.

34. An apparatus as defined in claim 29 wherein said spacer has an opening through which a tool extends to engage said fastener when said longitudinal member is disengaged from said spacer.

35. An apparatus as defined in claim 29 wherein said clamping mechanism includes a threaded member threadably engageable with said housing.

36. An apparatus as defined in claim 35 wherein said threaded member engages said longitudinal member to clamp said longitudinal member against said spacer.

37. An apparatus as defined in claim 35 wherein said threaded member and said housing have a buttress thread.

38. An apparatus comprising:

a longitudinal member connectable with a bone portion;

a fastener engageable with the bone portion having a longitudinal axis and connecting said longitudinal member to the bone portion;

a housing having a first passage through which said longitudinal member extends, said housing having a second passage with a longitudinal axis extending transverse to said first passage, said fastener extending through an opening in said housing into said second passage, said housing being movable relative to said fastener, said longitudinal axis of said second passage being positionable in any one of a plurality of angular positions relative to said longitudinal axis of said fastener;

a spacer received in said second passage of said housing and engageable with said fastener and said longitudinal member;

a member fixedly connected to said housing and extending from said housing into engagement with said spacer, said member applying an axial force to said spacer and holding said spacer in frictional engagement with said fastener, said member holding said longitudinal axis of said second passage of said housing in any one of said plurality of positions relative to said longitudinal axis of said fastener when said longitudinal member is disengaged from said spacer and said spacer engages said fastener, said fastener and said housing being manually movable relative to each other in opposition to said frictional engagement when said longitudinal member is disengaged from said spacer; and a clamping mechanism that clamps said longitudinal member, said spacer, and said housing to said fastener to prevent movement of said fastener relative to said housing.

\* \* \* \* \*